US008848341B2

(12) United States Patent
Sherwood

(10) Patent No.: US 8,848,341 B2
(45) Date of Patent: Sep. 30, 2014

(54) ELECTRONIC COMPONENT MOUNTED ON A CAPACITOR ELECTRODE

(75) Inventor: Gregory J. Sherwood, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 404 days.

(21) Appl. No.: 13/165,363

(22) Filed: Jun. 21, 2011

(65) Prior Publication Data

US 2011/0317370 A1    Dec. 29, 2011

Related U.S. Application Data

(60) Provisional application No. 61/358,099, filed on Jun. 24, 2010.

(51) Int. Cl.
| | |
|---|---|
| H01G 4/228 | (2006.01) |
| H01G 9/10 | (2006.01) |
| H05K 5/03 | (2006.01) |
| H01G 9/08 | (2006.01) |
| H01G 9/008 | (2006.01) |
| H01G 9/28 | (2006.01) |
| A61N 1/375 | (2006.01) |

(52) U.S. Cl.
CPC ............... *H01G 9/28* (2013.01); *A61N 1/3758* (2013.01); *H01G 9/08* (2013.01); *H01G 9/008* (2013.01)
USPC .......................................... 361/520; 361/538

(58) Field of Classification Search
USPC .................................................. 361/520, 538
See application file for complete search history.

(56) References Cited

U.S. PATENT DOCUMENTS

| | | | |
|---|---|---|---|
| 2,636,076 A | * | 4/1953 | Odvar et al. .................. 361/520 |
| 3,025,441 A | | 3/1962 | West |
| 3,331,759 A | | 7/1967 | Middelhoek et al. |
| 3,445,731 A | | 5/1969 | Saeki et al. |
| 3,627,520 A | | 12/1971 | Rogers |

(Continued)

FOREIGN PATENT DOCUMENTS

| | | |
|---|---|---|
| EP | 1470267 B1 | 4/2009 |
| JP | 02087512 A * | 3/1990 |
| JP | 04354114 A * | 12/1992 |

OTHER PUBLICATIONS

"U.S. Appl. No. 11/677,793, Final Office Action mailed May 19, 2010", 5 pgs.

(Continued)

*Primary Examiner* — David M Sinclair
(74) *Attorney, Agent, or Firm* — Schwegman Lundberg & Woessner, P.A.

(57) ABSTRACT

One example includes a capacitor case sealed to retain electrolyte, electrolyte disposed in the capacitor case, a capacitor electrode disposed in the capacitor case, an electronic component mounted to the capacitor electrode and disposed in the capacitor case, the electronic component including two contacts, with a first contact mounted onto the capacitor electrode and with a second contact mounted onto a terminal disposed on an exterior of the capacitor case and sealingly extending through the capacitor case, the first and second contacts electrically isolated from one another, a additional capacitor electrode disposed in the capacitor case, a separator disposed between the capacitor electrode and the additional capacitor electrode and a additional terminal disposed on the exterior of the capacitor case and in electrical communication with the additional capacitor electrode, with the terminal and the additional terminal electrically isolated from one another.

15 Claims, 8 Drawing Sheets

(56) References Cited

U.S. PATENT DOCUMENTS

| | | | |
|---|---|---|---|
| 3,638,083 A | 1/1972 | Dornfeld et al. | |
| 3,644,796 A | 2/1972 | Carino | |
| 3,647,415 A | 3/1972 | Yano et al. | |
| 3,789,502 A | 2/1974 | Callins et al. | |
| 4,059,116 A | 11/1977 | Adams | |
| 4,085,397 A | 4/1978 | Yagher | |
| 4,107,762 A | 8/1978 | Shirn et al. | |
| 4,118,753 A * | 10/1978 | Vind | 361/623 |
| 4,406,286 A | 9/1983 | Stein | |
| 4,442,473 A | 4/1984 | Holtzman et al. | |
| 4,635,163 A * | 1/1987 | Voglaire | 361/275.4 |
| 4,687,951 A | 8/1987 | McElroy | |
| 4,720,767 A | 1/1988 | Chan et al. | |
| 4,840,122 A | 6/1989 | Nerheim | |
| 4,882,115 A | 11/1989 | Schmickl | |
| 4,894,746 A | 1/1990 | Mori et al. | |
| 5,062,025 A | 10/1991 | Verhoeven et al. | |
| 5,097,404 A * | 3/1992 | Layh | 363/146 |
| RE34,879 E | 3/1995 | Bocchi et al. | |
| 5,424,909 A * | 6/1995 | Kuriyama | 361/534 |
| 5,468,254 A | 11/1995 | Hahn et al. | |
| 5,591,211 A | 1/1997 | Meltzer | |
| 5,591,217 A | 1/1997 | Barreras | |
| 5,634,938 A | 6/1997 | Swanson et al. | |
| 5,763,911 A | 6/1998 | Matthews et al. | |
| 5,807,397 A | 9/1998 | Barreras | |
| 5,874,770 A | 2/1999 | Saia et al. | |
| 5,930,109 A | 7/1999 | Fishler | |
| 6,115,235 A | 9/2000 | Naito | |
| 6,161,040 A | 12/2000 | Blunsden | |
| 6,193,779 B1 | 2/2001 | Reichert et al. | |
| 6,219,221 B1 * | 4/2001 | Kibi et al. | 361/502 |
| 6,241,751 B1 | 6/2001 | Morgan et al. | |
| 6,310,757 B1 | 10/2001 | Tuzuki et al. | |
| 6,347,032 B2 | 2/2002 | Naito | |
| 6,350,406 B1 | 2/2002 | Satou et al. | |
| 6,351,371 B1 * | 2/2002 | Yoshida et al. | 361/528 |
| 6,385,031 B1 | 5/2002 | Lerche et al. | |
| 6,456,877 B1 | 9/2002 | Fishler | |
| 6,699,265 B1 | 3/2004 | O'Phelan et al. | |
| 6,775,127 B2 | 8/2004 | Yoshida | |
| 6,778,860 B2 | 8/2004 | Ostroff et al. | |
| 6,785,123 B2 | 8/2004 | Keser | |
| 6,801,424 B1 | 10/2004 | Nielsen et al. | |
| 6,807,048 B1 | 10/2004 | Nielsen et al. | |
| 6,850,405 B1 | 2/2005 | Mileham et al. | |
| 6,855,234 B2 | 2/2005 | D'Astolfo, Jr. | |
| 6,865,417 B2 | 3/2005 | Rissmann et al. | |
| 6,952,608 B2 | 10/2005 | Ostroff | |
| 6,954,670 B2 | 10/2005 | Ostroff | |
| 7,024,246 B2 | 4/2006 | Acosta et al. | |
| 7,327,557 B2 | 2/2008 | Poplett | |
| 7,522,957 B2 | 4/2009 | Ostroff | |
| 7,760,488 B2 | 7/2010 | Breznova et al. | |
| 7,856,265 B2 | 12/2010 | Linder et al. | |
| 8,364,259 B2 | 1/2013 | Linder et al. | |
| 2006/0035152 A1 | 2/2006 | Nishimura et al. | |
| 2007/0109723 A1 | 5/2007 | Kuriyama et al. | |
| 2007/0109727 A1 | 5/2007 | Edson et al. | |
| 2008/0030927 A1 * | 2/2008 | Sherwood | 361/520 |
| 2008/0198534 A1 | 8/2008 | Lee et al. | |
| 2008/0208270 A1 | 8/2008 | Linder et al. | |
| 2009/0231782 A1 | 9/2009 | Fujita et al. | |
| 2009/0237862 A1 | 9/2009 | Nielsen et al. | |
| 2009/0242415 A1 | 10/2009 | Yoshimitsu | |
| 2009/0273884 A1 | 11/2009 | Shimizu et al. | |
| 2010/0010562 A1 | 1/2010 | Daley et al. | |
| 2010/0110614 A1 | 5/2010 | Umemoto et al. | |
| 2010/0110615 A1 | 5/2010 | Nishimura et al. | |
| 2010/0157510 A1 | 6/2010 | Miyachi et al. | |
| 2010/0193731 A1 | 8/2010 | Lee et al. | |
| 2010/0195261 A1 | 8/2010 | Sweeney et al. | |
| 2010/0226066 A1 | 9/2010 | Sweeney et al. | |
| 2010/0226070 A1 | 9/2010 | Yang et al. | |
| 2011/0066199 A1 | 3/2011 | Linder et al. | |
| 2011/0152961 A1 | 6/2011 | Sherwood | |

OTHER PUBLICATIONS

"U.S. Appl. No. 11/677,793, Non-Final Office Action mailed Sep. 29, 2009", 12 pgs.

"U.S. Appl. No. 11/677,793, Notice of Allowance mailed Aug. 11, 2010", 8 pgs.

"U.S. Appl. No. 11/677,793, Response filed Jan. 28, 2010 to Non-Final Office Action mailed Sep. 29, 2009", 16 pgs.

"U.S. Appl. No. 11/677,793, Response filed Jun. 15, 2009 to Restriction Requirement mailed May 13, 2009", 10 pgs.

"U.S. Appl. No. 11/677,793, Response filed Jul. 19, 2010 to Final Office Action mailed May 19, 2010", 10 pgs.

"U.S. Appl. No. 11/677,793, Restriction Requirement mailed May 13, 2009", 10 pgs.

Bocek, Joseph M, et al., "Method and Apparatus for Charging Partitioned Capacitors", U.S. Appl. No. 11/462,301, filed Aug. 3, 2006, 53 pgs.

"U.S. Appl. No. 12/952,554, Non Final Office Action mailed Jun. 18, 2012", 7 pgs.

"U.S. Appl. No. 12/952,554, Notice of Allowance mailed Oct. 1, 2012", 8 pgs.

"U.S. Appl. No. 12/952,554, Response filed Jun. 4, 2012 to Restriction Requirement mailed May 4, 2012", 8 pgs.

"U.S. Appl. No. 12/952,554, Response filed Sep. 18, 2012 to Non Final Office Action mailed Jun. 18, 2012", 13 pgs.

"U.S. Appl. No. 12/952,554, Restriction Requirement mailed May 4, 2012", 7 pgs.

"U.S. Appl. No. 12/968,584, Response filed Oct. 29, 2013 to Non Final Office Action mailed Jul. 31, 2013", 10 pgs.

"U.S. Appl. No. 12/968,584, Non Final Office Action mailed Jan. 30, 2013", 11 pgs.

"U.S. Appl. No. 12/968,584, Non Final Office Action mailed Jul. 31, 2013", 12 pgs.

"U.S. Appl. No. 12/968,584, Response filed Apr. 26, 2013 to Non Final Office Action mailed Jan. 30, 2013", 10 pgs.

* cited by examiner

ELECTRONIC COMPONENT MOUNTED ON A CAPACITOR ELECTRODE

CROSS-REFERENCE TO RELATED APPLICATIONS

This application claims the benefit of U.S. Provisional Application No. 61/358,099, filed on Jun. 24, 2010, under 35 U.S.C. §119(e), which is incorporated herein by reference in its entirety.

TECHNICAL FIELD

This document relates generally to energy storage and particularly to at least one electronic component mounted on an electrode such as a capacitor electrode used in a cardiac defibrillator.

BACKGROUND

Capacitors both store and discharge electrical energy quickly. In storing or discharging, electrical energy is transferred through subcomponents of the capacitor. Inefficiencies such as poor conductivity between subcomponents can result in undesirable performance. Poor performance includes undesirable heating, or undesirably slow charging or discharging. Compensating for poor performance in some instances translates to a capacitor that is undesirably upsized. Capacitors and other power sources can benefit from improved performance, which can at least enable cooler operating, smaller capacitors.

SUMMARY

This document relates to energy storage devices such as capacitors that include one or more electronic components, such as resistors or diodes, mounted onto an electrode. Electronic components include passive components and active components. Examples include electronic components mounted onto an electrode and disposed inside a case such as a capacitor case. Some examples including electrolyte disposed inside the case. In some of these examples, electrolyte surrounds the electronic component. In some configurations, the components are potted wherein their contacts do not short to one another.

There are several improvements provided by the systems, apparatus and methods discussed here. For example, by mounting an electronic component on a capacitor electrode, the electrical resistance experienced by a charge stored as it moves from storage to the electronic component is reduced. For example, electrons moving from storage to a switch mounted onto an electrode pass experience less electrical resistance than those that move from storage to a switch that is not mounted on an electrode, that is, one that is mounted to an electrical circuit that is coupled to the electrode. Generally, examples discussed here provide lower equivalent series resistance ("ESR"). Accordingly, some examples operate at lower temperatures.

There are a number of benefits from capacitors that operate at lower temperatures. One benefit is that the capacitor has an improved thermal mass. As such, the capacitor has an increased capacity to sink heat away from components coupled to the capacitor, such as switches. Also, capacitors that operate at lower temperatures, or with smaller changes in temperature, experience reduced thermal shock. Reductions in thermal shock can improve reliability. Also, if the capacitor has reduced resistance, and a predetermined amount of temperature change is tolerable, the capacitor can thus withstand increased charging or discharging rates as well.

An additional benefit of this technology is that capacitors can be efficiently manufactured, which can ultimately lower costs for consumers. For example, electronic components can be installed on capacitor electrodes during manufacture of the electrode, which can alleviate the need for interconnecting circuit boards. Positioning electronics components on electrodes also reduces the need to handle and install these components in downstream manufacturing processes.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment.

The following detailed description is, therefore, not to be taken in a limiting sense, and the scope is defined only by the appended claims, along with the full scope of legal equivalents to which such claims are entitled.

Electronic components, as described herein, are those other than the capacitor electrode. In various examples, mounting includes conductively mounting to both physically affix the electronic component to the electrode as well as place the electronic component into electrical communication with the electrode. Accordingly, the electrode portion of the capacitor is electrically coupled to a portion of the electronic component that is not part of the electrode, such as a resistive portion of a resistor, a switch portion of a switch, etc. Mounting, in some examples, refers to thermally mounting electronics components, which includes physically affixing the electronic component to the electrode with the electronic component in thermal conductivity with the electrode. Some examples discuss electrode technology, such as sintering, that complements disposing electronic components onto an electrode. Several example circuits that are enabled by this technology are discussed. This application is not limited to electronic components that are resistors or diodes, and includes other electronic components including, but not limited to, switches, fuses, sensors, transformers, inductors and other electronic components. Additionally, methods of making and methods of using such devices are discussed.

Figure 1:
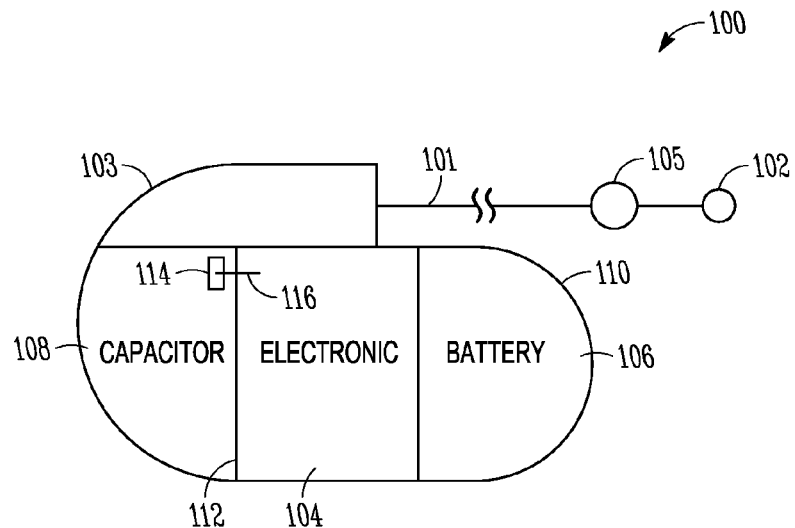
FIG. 1 is a diagram of a medical system including a capacitor with an electronic component mounted on an electrode, according to various examples.

FIG. 1 is a diagram of a medical system including a capacitor with an electronic component mounted on an electrode, according to various examples. The medical system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators such as automatic external defibrillators.

In various examples, electronics 104 are to monitor the patient, such as by monitoring a sensor 105, and to monitor and control activity within the medical system 100. In some examples, the electronics 104 are to monitor a patient, diagnose a condition to be treated such as an arrhythmia, and control delivery of a stimulation pulse of energy to the patient. In some instances, electronics 104 are powered wirelessly using an inductor. In additional configurations, the electronics 104 are powered by a battery 106. In some examples, electronics 104 are to direct small therapeutic bursts of energy from the battery 106 to a patient.

For therapies that use energy discharge rates exceeding what battery 106 is able to provide, such as defibrillation, a capacitor 108 is used. Energy from the battery 106 is controlled by the electronics 104 to charge the capacitor 108. The capacitor 108 is controlled with the electronics 104 to discharge to a patient to treat the patient. In some examples, the capacitor 108 completely discharges to a patient, and in additional examples, the capacitor 108 is switched on to provide therapeutic energy and switched off to truncate therapy delivery.

Some examples of a medical system 100 include an optional lead system 101. In certain instances, after implantation, the optional lead system 101 or a portion of the optional lead system 101 is in electrical communication with tissue to be stimulated. For example, some configurations of optional lead system 101 contact tissue with a stimulation electrode 102. The optional lead system 101 couples to other portions of the medical system 100 via a connection in a header 103. Examples of the system 101 use different numbers of stimulation electrodes and/or sensors in accordance with the needs of the therapy to be performed.

Additional examples function without a lead 101 and are leadless. Leadless examples are positioned in contact with the tissue to be stimulated, or are positioned proximal to a tissue to be stimulated to shock the tissue through intermediary tissue. In some examples, leadless systems are easier to implant and are less expensive as they do not use additional lead components. Hermetically sealed device housing 110 is used as an electrode in leadless configurations, in some examples.

In certain examples, the electronics 104 include an electronic cardiac rhythm management circuit coupled to the battery 106 and the capacitor 108 to discharge the capacitor 108 to provide a therapeutic defibrillation pulse. In some examples, the medical system 100 includes an anode and a second electrode such as a cathode sized to deliver a defibrillation pulse of at least approximately 50 joules. This energy level is predetermined to achieve a delivered energy level mandated by a governing body or standard associated with a geographic region, such as a European country. In an additional example, the anode and second electrode are sized to deliver a defibrillation pulse of at least approximately 60 joules. This energy level is predetermined to achieve an energy level mandated by a governing body of another region, such as the United States. In some examples, electronics 104 are to control discharge of a defibrillation pulse so that the medical system 100 delivers only the energy mandated by the region in which the medical system 100 is used.

Packaging anodes and cathodes can reduce their efficiency. Interconnections between conductors coupled to electronics 104 and to the electrodes of the capacitor 108 decrease efficiency of charging and discharging, for example. Accordingly, anodes and cathodes are sized to compensate for decreases in efficiency. As such, in various examples, the capacitor 108 includes anodes and second electrodes sized and packaged to deliver a defibrillation pulse of at last approximately 50 joules. Some are sized and packaged to deliver a defibrillation pulse of at least approximately 60 joules. Some examples mount electronic components on an electrode to reduce equivalent series resistance, improving operational efficiency.

Several examples include electrodes that are at least partially sintered. One characteristic of some sintered electrode examples is that at least one anode and at least one cathode have a DC capacitance that is approximately 23% greater than an AC capacitance for the at least one anode and the second electrode. In some examples, the at least one anode and the second electrode have an AC capacitance of at least 96.7 microfarads per cubic centimeter at 445 total voltage. This is a 30% improvement over an etched capacitor that has 74.5 microfarads per cubic centimeter. Total voltage is the voltage that allows 1 milliamp of leakage per square centimeter. Some examples are aged to 415 volts.

In certain examples, the capacitor 108 includes a capacitor case 112 sealed to retain electrolyte. In some examples, the capacitor case 112 is welded to seal the case. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal. Several materials can be used to form capacitor case 112, including, but not limited to, aluminum, titanium, stainless steel, nickel, a polymeric material, or combinations of these materials. The capacitor case 112 is sealed to retain electrolyte. Various electrolytes can be used including, but not limited to, Suzuki- Techno Corporation electrolyte model 1184. The capacitor case 112 includes a seal, such as a resin-based seal including but not limited to epoxy, in some examples. Some examples include a rubber seal to seal case portions to one another, or to seal subcomponents such as a feedthrough to one or more case portion. In some examples, capacitor case 112 is welded together from subcomponents. Some examples include a case that includes one or more backfill ports, but the present subject matter is not so limited.

The hermetically sealed device housing 110 is used to house components, such as the battery 106, the electronics 104, and the capacitor 108. Hermeticity is provided by welding components into the hermetically sealed device housing 110 in some examples. Other examples bond portions of the device housing 110 together with an adhesive such as a resin-based adhesive such as epoxy. Accordingly, some examples of the device housing 110 include an epoxy sealed seam or port. Several materials can be used to form device housing 110, including, but not limited to, titanium, stainless steel, nickel, a polymeric material, or combinations of these materials. In various examples, the device housing 110 and the capacitor case 112 are biocompatible.

The capacitor 108 is improved by the present electrode technology in part because it can be made smaller and with less expense. The improvement provided by these electrodes is pertinent to any application where high-energy, high-voltage, or space-efficient capacitors are desirable, including, but not limited to capacitors used for photographic flash equipment. The present subject matter extends to energy storage devices that benefit from high surface area sintered electrodes including, but not limited to, aluminum. The electrodes described here can be incorporated into cylindrical capacitors that are wound, in addition to stacked capacitors. Some examples include electrodes in a slug configuration. For example, in some examples, the anode of a capacitor comprises one or more slugs. In some examples, a slug comprises sintered material disposed on a foil substrate.

Some examples include an electronic component 114 mounted onto a capacitor electrode of the capacitor 108. The electronic component 114 is mounted in an electrically conductive manner. Mounting configurations contemplated physically fix the electronic component 114 onto the electrode, such as by welding, soldering or by fixation with an adhesive such as an electrically conductive polymer. In some examples, the electronic component 114 is disposed in the capacitor case 112 and coupled to a terminal 116 extending out of the case.

Figure 2:
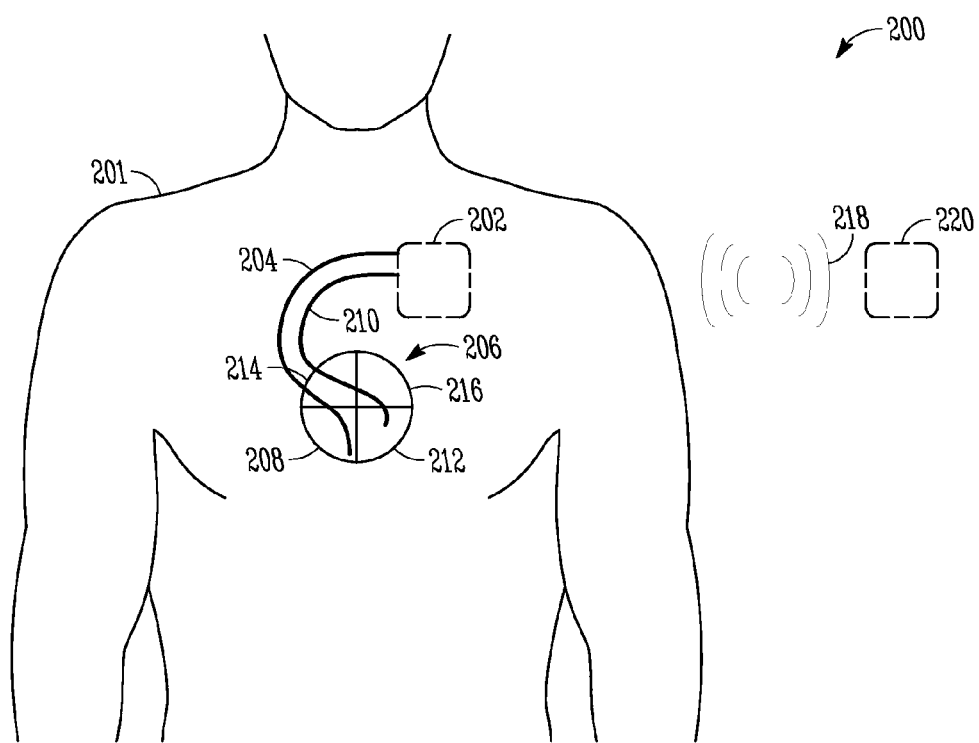
FIG. 2 is an implanted medical system including a capacitor including an electronic component mounted to an electrode, according to various examples.

FIG. 2 is an implanted medical system including a capacitor including an electronic component mounted to an electrode, according to various examples. The system 200 includes a cardiac rhythm management device 202 coupled to a first lead 204 to extend through the heart 206 to the right ventricle 208 to stimulate at least the right ventricle 208. The system 200 also includes a second lead 210 to extend through the heart 206 to the left ventricle 212. In various examples, one or both of the first lead 204 and the second lead 210 include electrodes to sense intrinsic heart signals and to stimulate the heart 206. The first lead 204 is in direct contact (e.g., touching) with the right atrium 214 and the right ventricle 208 to sense and/or stimulate both of those tissue regions. The second lead 210 is in direct contact with the left atrium 216 and the left ventricle 212 to sense and/or stimulate both those tissue regions. The cardiac rhythm management device 202 uses the lead electrodes to deliver energy to the heart 206, between electrodes on the leads 204 and 210 or between one or more lead electrodes and the cardiac rhythm management device 202. In some examples, the cardiac rhythm management device 202 is programmable and wirelessly 218 communicates programming information with a programmer 220. In some examples, the programmer 220 wirelessly 218 charges an energy storage device of the cardiac rhythm management device 202. Other stimulation topologies, such as those that stimulate other portions of the body 201, additionally benefit from the one or more electronic components mounted to electrodes, and the associated disclosed herein.

Figure 3A:
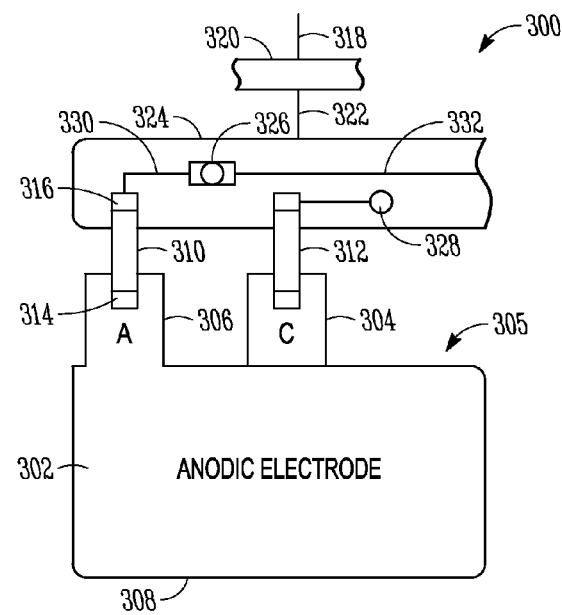
FIG. 3A is a plan view of a portion of a capacitor including electronic components mounted to an electrode and to an electrical bus, according to various examples.
Figure 3B:
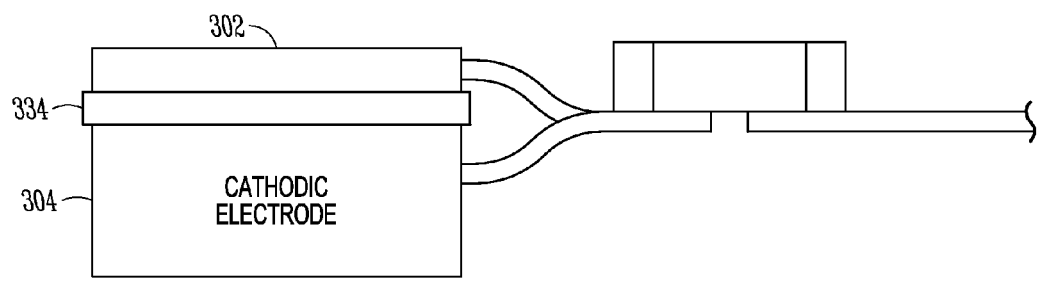
FIG. 3B is a right side view of the capacitor of FIG. 3A.

FIG. 3A is a plan view of a portion of a capacitor including electronic components coupled to an electrode and to an electrical bus, according to various examples. FIG. 3B is a right side view of the capacitor of FIG. 3A. In various examples, the assembly 300 is disposed in a capacitor case, such as the capacitor case 112 illustrated in FIG. 1. The assembly 300 includes at least one anodic electrode 302. The assembly 300 additionally includes a cathodic electrode 304. The anodic electrode 302 is stacked into a stack 305 with the cathodic electrode 304 in some examples. In some examples, a separator 334 is disposed between the anodic electrode 302 and the cathodic electrode 304. In additional examples, one or both the anodic electrode 302 and the cathodic electrode 304 comprise a slug.

In certain examples, an anodic electrode 302 includes an anodic connection member 306. Accordingly, the anodic connection member 306 forms part of the anode. In some examples, a cathodic electrode includes a cathodic connection member. Accordingly, the cathodic connection member forms part of the cathode electrode. In some examples, the anodic connection member 306 extends away from a main body 308 of the stack 305. Some examples include a number of anodes stacked onto one another, with respective edges aligned to define a connection surface for interconnecting the anodes. In some examples, at least one capacitor electrode defines a sheet. For instance, anodic electrode 302 is sheet-shaped in some examples. In some examples, one or both of the anodic electrode 302 and the cathodic electrode 304 are formed of foils. In some examples, one or both of the anodic electrode 302 and the cathodic electrode 304 includes foils with sintered material formed onto at least a portion of the foil, as set forth in U.S. Provisional Patent Application Ser. No. 61/288,062, filed Dec. 18, 2009, commonly assigned and incorporated herein by reference in its entirety. In various examples, a sintered portion of an electrode is disposed on a foil substrate, and an electronic component is mounted on the foil substrate. The foil substrate's flexibility at least in part enables mounting of the electronic component. In some examples, the foil substrate is thick enough to withstand welding or soldering to enable mounting of an electronic component. This is in contrast to an etched foil, which may break during welding or soldering, or which otherwise might suffer a reduced surface area, and an associated reduction in performance. In some examples, an electronic component 310 is disposed on a connection member, with two contacts of the electronic component 310 disposed on the connection member, with the connection member excised to electrically isolate the contacts of the electronic component 310. Examples of excision include laser cutting.

In various examples one or more electronic components are mounted onto an electrode. For example, an electronic component 310 is mounted onto the anodic electrode 302. A additional electronic component 312 is mounted onto the cathodic electrode 304. Additional examples mount electronic components only to anodic electrodes, with the capacitor including cathodes that do not have electronic components mounted onto them, and vice versa. Electronic components include diodes, resistors and switches, for example.

In certain examples, an electronic component includes at least two contacts, with a first contact mounted onto at least one capacitor electrode. For example, the electronic component 310 includes a first contact 314 and a second contact 316. Conductive coupling includes welding, soldering and the like, including, but not limited to, adhesion with conductive adhesive such as conductive polymer. In various examples, a second contact 316 is conductively coupled with a terminal 318 disposed on an exterior of the capacitor case 320 (shown in cross section). In certain examples, a conductor 322 that is ultimately coupled to the electronic component 310 inside the capacitor case 320 sealingly extends through the capacitor case 320.

In various examples, the first 314 and second 316 contacts are electrically isolated from one another. In some examples, this is through air insulation. In some examples, the case 320 is filled with electrolyte. Because electrolyte is conductive, these examples include electrical insulation to isolate the first contact 314 from the second contact 316. Electrical insulation includes, but is not limited to, dielectric coatings and potting.

Various examples include an interconnect 324 to connect to one or more electronic components 310. In some examples, the interconnect 324 is a metallic bus such as a busbar. In some examples, the interconnect 324 is ribbon shaped. In additional examples, the interconnection 324 is a circuit board. Circuit boards include, but are not limited to, stiff circuit boards such as boards formed of fiberglass, flexible circuit boards such as circuit boards formed of polyimide, and hybrid circuit boards formed of stiff portions and flexible portions.

In various examples, one or more components of the assembly 300 are mounted on the interconnect 324, and additional components are electrically isolated from conductive portions of the interconnect 324, such as mounting pads, vias and traces. The interconnect 324 is electrically isolated from the additional components through electrically isolating coating, potting and the like, in various examples.

In some examples, the illustrated interconnect 324 includes one or more additional electronic components 326, 328 mounted on it, such as resistors or diodes. Accordingly, in some examples, an electrical circuit includes an anodic electrode 302, the electronic component 310, conductors 322, 330 and 332, an additional electronic component 326 and the terminal 318. Additionally, the conductor 332 can optionally connect to additional electronics, including electronics optionally mounted on the interconnect 324.

In some examples, one or more electronic components are mounted to a mating part using surface mount technology ("SMT"). Some examples mount one or more electronic components using vias or through-hole mounting. Other mounting styles are possible, including riveting, stapling and other mounting configurations.

Figure 4:
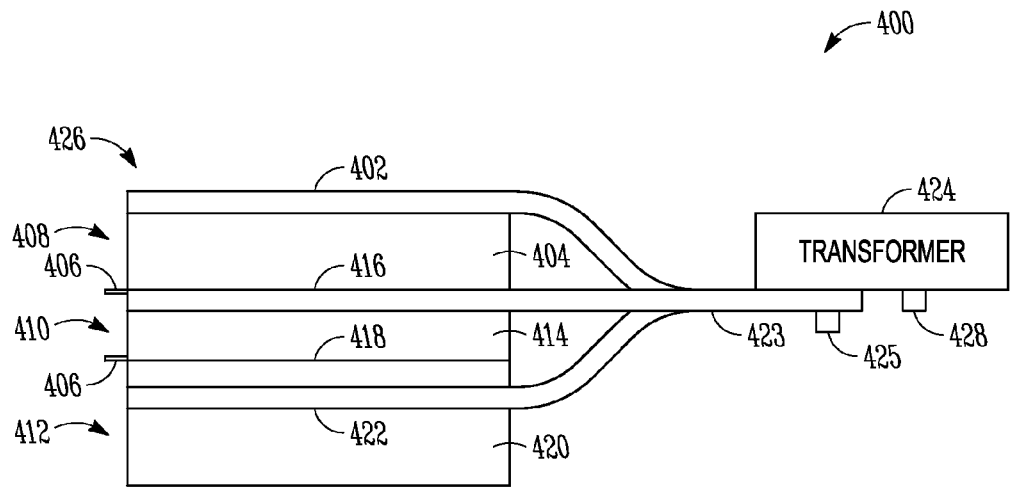
FIG. 4 is a right side view of a portion of a capacitor including a transformer mounted to an electrode, according to various examples.

FIG. 4 is a right side view of a portion of a capacitor including a transformer mounted to an electrode, according to various examples. The assembly 400 includes at least one anode comprised of a flexible substrate 402 coupled with sintered material 404. Flexible substrates are bendable without breaking. Bending includes elastic and inelastic deformation. In some examples the flexible substrate 402 is a foil, but the present subject matter is not so limited. The assembly 400 is part of a capacitor that has improved performance and that is easier to manufacture. Performance is improved at least because of sintering, which provides an increase in functional surface area of an electrode. The assembly 400 is easier to manufacture because the sintering is coupled with a flexible substrate 402. This substrate 402 is bendable. In some examples, the flexible substrate 402 is bendable even after the assembly 400 has been aged and has one or more electrodes coated with oxidation that can be brittle. In some examples, separator 406 is used to separate a first electrode 408 from a second electrode 410, but other examples are possible, including examples that use physical spacers such as cradles to separate one or more electrodes. According to various examples, a first electrode 408 is anodic and a second electrode 410 is cathodic. The second electrode 410 is shown including sintered material 414 coupled to a flexible substrate 416 such as a foil, but the present subject matter is not so limited. For example, some configurations include a cathodic substrate that is not sintered. In some examples, the cathodic substrate is flexible. In some examples it is foil. Some examples include an anode 412 with sintered material on two sides, 418, 420 of a foil substrate 422.

In the illustrated example, a number of foils are pressed together into a connection member 423 that includes one or more layers of electrode connection members. The connection member 423 is to attach to an electronic component, and optionally to attach to other components, such as one or more conductors of a feedthrough. The illustrated electronic component is a transformer 424 having a terminal 425 mounted through a through-hole in the connection member 423. The transformer 424 in some examples is soldered to the connection member 423. Accordingly, the transformer 424 is conductively coupled to the connection member 423. In some examples, the transformer 424 is thermally coupled to the connection member 423, which enables the stack of electrodes 426 to operate as a heat sink to dissipate heat from the transformer 424 in operation. In some examples, the connection member 423 is bent with the height of the transformer 424 parallel to the height of the stack of electrodes 426. By packaging the transformer 424 as such, in some examples, the overall height of a device using the assembly 400 is reduced. Height is reduced because in some devices the transformer 424 is the single tallest component, and by reducing the need for the transformer 424 to connect to a circuit board, the height of the device can be reduced. In some examples, the transformer 424 includes one or more additional terminals 428. In various examples, these additional terminals 428 are electrically insulated from the terminal 425. Examples of electrical insulation include coating and potting materials.

Figure 5:
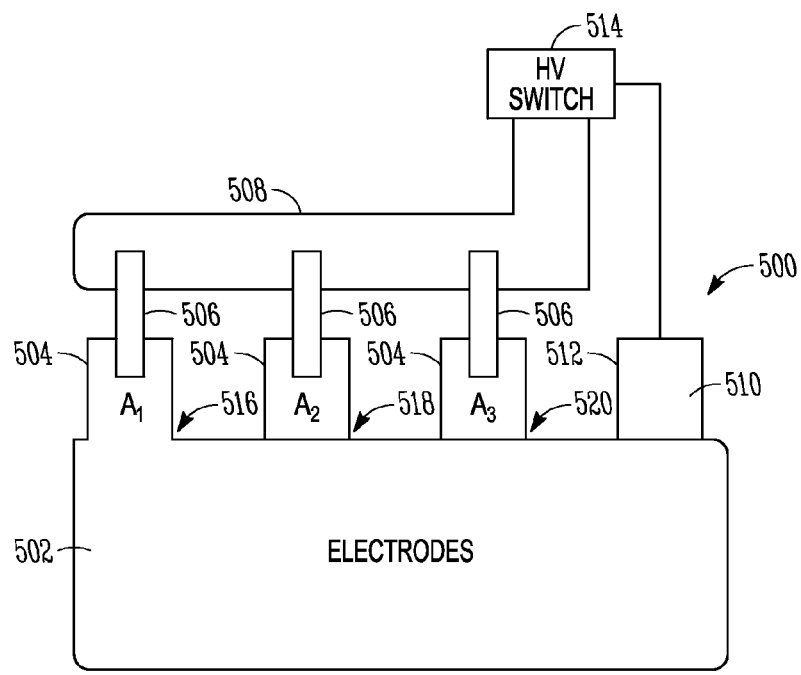
FIG. 5 is a diagram of a capacitor including electronic components mounted to respective electrodes, according to various examples.
Figure 6:
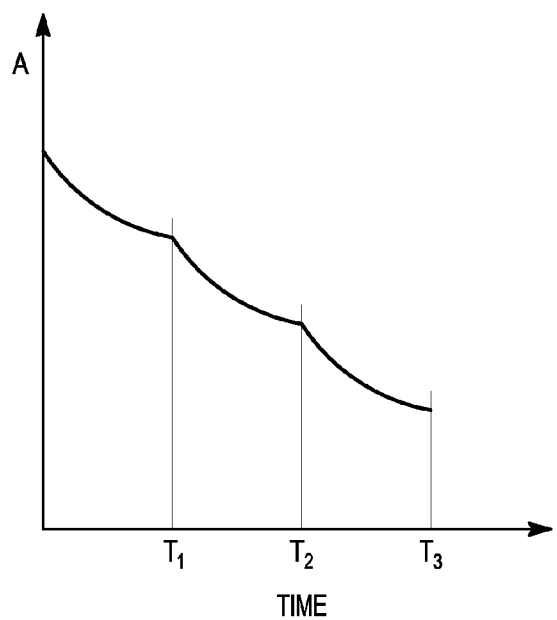
FIG. 6 is a chart of amperage over time for the capacitor of FIG. 5.

FIG. 5 is a diagram of a capacitor including electronic components mounted to respective electrodes, according to various examples. FIG. 6 is a chart of amperage over time for the capacitor of FIG. 5. The assembly 500 pictured in FIG. 5 is a stack of electrodes 502 including anodic electrodes $A_1$, $A_2$, and $A_3$, each including a connection member 504. In various examples, the stack of electrodes 502 includes electrodes with aluminum sintered onto aluminum foil, but the present subject matter is not so limited. Each of the connection members 504 include electronic components 506 mounted thereon. The pictured electronic components 506 are diode, but the present subject matter is not so limited. Each of the electronic components 506 is mounted onto a conductive interconnect 508. In some examples, the conductive interconnect 508 is a busbar. Additional examples include flex circuit, metallic ribbon, a conductive portion of a case for the assembly 500 and other conductive interconnects. In various examples, the electronic components 506 include a first contact mounted to a connection member of an electrode, and a second contact mounted to the conductive interconnect 508, with the first contact and the second contact electrically isolated from one another. A cathode 510 is pictured. The cathode 510 optionally includes a connection member 512, but the present subject matter is not so limited. In some examples, the cathode connection member 512 is coupled to a conductive portion of a capacitor case, with the conductive portion of the capacitor case then connected to other electronics, such as a high voltage switch.

In various examples, the conductive interconnect 508 is coupled to a high voltage switch 514 to control discharge of the electrodes 502. The high voltage switch 514 is connected to other components. In some examples, the high voltage switch 514 is coupled to shocking electrodes in a defibrillation system.

In various examples, the electrodes 502 are configured in partitions. For example, some examples include a first capacitor partition 516 that is adapted to discharge in sequence with the second capacitor partition 518. In some examples, the electronic components 506 enable sequential discharge. FIG. 6 illustrates an amperage of a capacitor such as the capacitor assembly 500. The first partition 516 discharges until, for example at time T1, the discharge voltage is low enough to allow another partition, such as the second partition 518, to discharge. In some examples, at time T2, the second partition has reached a voltage low enough to enable a third partition 520 to discharge. At time T3, the high voltage switch 514 truncates discharge. Optionally, the assembly 500 is allowed to discharge until stasis with a load to which the assembly 500 is conductively connected, such as shocking electrodes.

Figure 7:
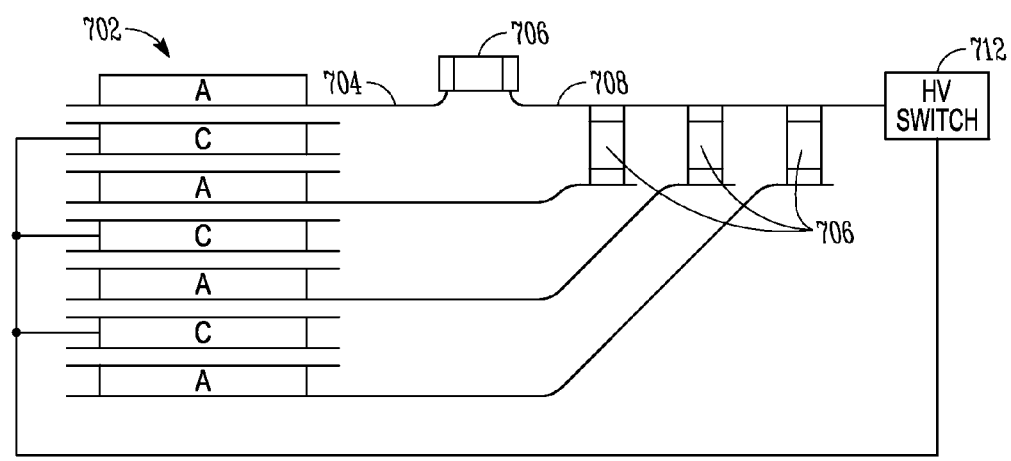
FIG. 7 is a side view of a portion of a capacitor including electronic components mounted horizontally to a bus, according to various examples.

FIG. 7 is a side view of a portion of a capacitor including electronic components mounted horizontally to a bus, according to various examples. The side view shows some of the mechanical benefits the present subject matter offers. A stack of electrodes 702 includes anodes marked "A," cathodes marked, "C" and separators disposed between the anodes and the cathodes. In various examples, the anodes include substrates 704. In some examples, the substrates include foil. Electronic components 706 are mounted onto the substrates 704 such as by surface mounting. In the illustrated example, each of the anodes has an electronic component 706 mounted thereon, with each of the electronic components 706 mounted onto a conductive interconnect 708. In some examples, the conductive interconnect 708 and each of the electronic components 706 is electrically insulated from its surrounding, such as through potting. The anodes and one or more cathodes 710 are coupled to a high voltage switch 712 that is in turn coupled to other components, such as shocking electrodes. The high voltage switch 712 is controlled to discharge charge stored in the electrodes 702 to a load such as a heart.

In some examples, each of the electronic components 706 is first mounted onto the conductive interconnect 708 and then mounted onto an electrode 702. In additional examples, electronic components 706 are mounted onto respective electrodes 702 and then are mounted onto a conductive interconnect 708. In some examples, electronic components 706 are mounted onto one side of a conductive interconnect 708. In additional examples, electronic components are mounted onto two sides of a conductive interconnect. In examples where electronics are mounted on one side of a conductive interconnect, traditional manufacturing methods such as pick-and-place manufacturing can be used to position electronic components in place. After electronic components are in place, one or more connection members are bent into position if desired. In some examples, the electronic components and the structures to which they are mounted are electrically insulated, such as by potting. In some examples, the electronic components and a conductive interconnect are aged.

Figure 8:
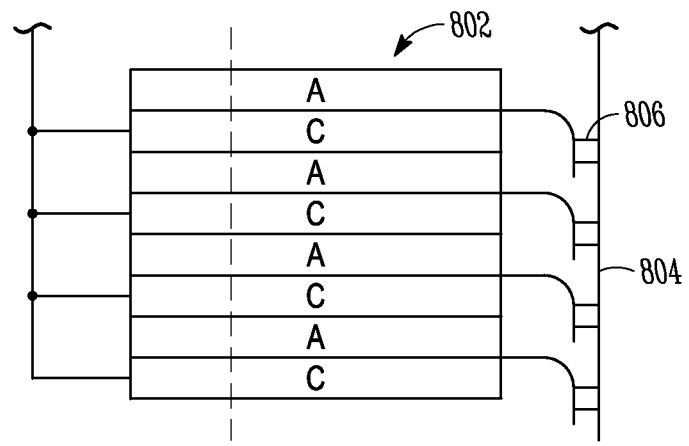
FIG. 8 is a side view of a portion of a capacitor including electronic components mounted vertically to a bus, according to various examples.

FIG. 8 is a side view of a portion of a capacitor including electronic components mounted vertically to a bus, according to various examples. A stack 802 of electrodes is illustrated, showing anodes and cathodes in a stack. In some examples, separator is disposed between each anode and an adjacent electrode of opposite polarity in use. In the illustration, for reference, the stack 802 is stacked in a vertical direction. In various examples, a conductive interconnect 804 extends along the stack 802 and is disposed in a vertical plane. Electronic components 806 are mounted onto electrodes of the stack 802 and the conductive interconnect 804. Interconnection of cathodes is represented schematically and can be via conductors, a busbar, connection members that are folded together, or using other interconnection methods.

The figure is a diagrammatic example of a capacitor stacked into a capacitor case and including electronics mounted onto electrodes and mounted to the capacitor case. Some examples include a capacitor case that serves as a conductive interconnect 804. In some examples, the capacitor case includes two electrically conductive portions that are electrically isolated from one another, with anodes coupled to a first portion and cathodes coupled to a second portion. In some examples, the capacitor case is includes a dish portion and lid portion, with the electronic component mounted onto the dish portion.

Figure 9:
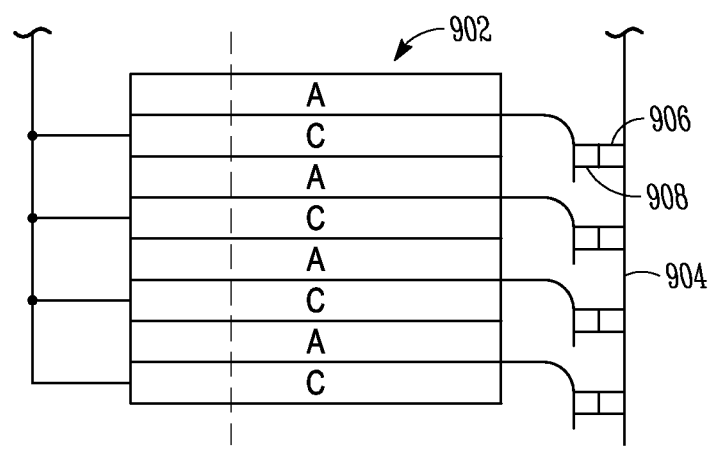
FIG. 9 is a side view of a portion of a capacitor including multiple electronic components mounted vertically to a bus, according to various examples.

FIG. 9 is a side view of a portion of a capacitor including multiple electronic components mounted vertically to a bus, according to various examples. The illustration shows an example in which two electronic components are mounted together in a set. Each electronic component set is both mounted to an electrode of an electrode stack 902 and mounted to a conductive interconnect 904, such as a busbar or a capacitor case. In some examples, the electronic component set includes a diode 906 coupled to a resistor 908. In some examples, an anode of the diode 906 is coupled to the resistor 908, which is coupled to a capacitor electrode and a cathode of the diode 906 coupled with the conductive interconnect 904.

Figure 10:
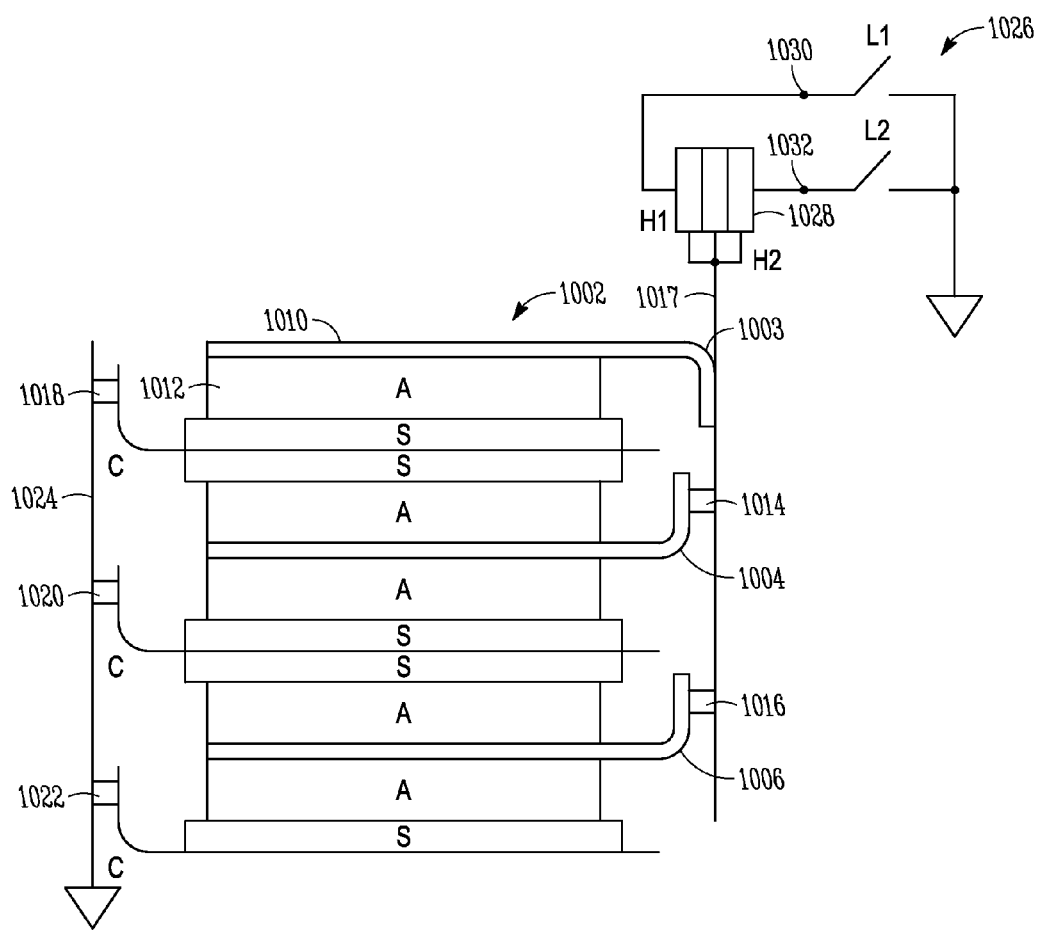
FIG. 10 is a side view of a partial schematic and a portion of a capacitor, including high side switches thermally conductive to a capacitor electrode, according to various examples.

FIG. 10 is a side view of a partial schematic and a portion of a capacitor, including high side switches thermally conductive to a capacitor electrode, according to various examples. A stack 1002 of electrodes is illustrated, with anodes denoted as "A," cathode denoted as "C," and separators denoted with "S." Although the present disclosure is not so limited, the anodes include respective foil substrates 1010, with one or more sintered portions 1012 disposed on at least one side of the foil substrate. Some examples include sintered material disposed on two sides of a foil substrate, in part to ensure that sintering does not roll the foil due to thermal inequalities during the sintering process.

Among the stack 1002, at least one electrode has a connection member 1003. Some examples include a first anode with a connection member 1003, a second anode with a second connection member 1004, and a third conductive anode with a third connection member 1006. In the illustrated example, cathodes include respective connection members. The cathodes illustrated are thinner than the anodes, in part because this bias in surface area results in improved performance.

In various examples, electronic components 1014 and 1016 are mounted onto respective connection members 1004, 1006. In some examples, electronic components 1014 and 1016 are switches, such as solid state switches, to control conductivity between respective electrodes and the conductive interconnect 1017.

In additional examples, electronic components 1018, 1020, and 1022 are mounted to respective connection members of cathodes. In various examples, these electronic components 1018, 1020, 1022 are switches, such as solid state switches, to control conductivity between respective cathode and a cathodic conductive interconnect 1024. The cathodic conductive interconnect 1024 is shown coupled to ground, but the present subject matter is not so limited.

Additionally illustrated is an H-bridge circuit 1026 including low side switches L1 and L2, and high side switches H1 and H2. The H-bridge circuit 1026 is to reverse polarity of a discharge waveform in some examples, and serves to direct energy to the nodes 1030 and 1032. In some examples, the nodes 1030 and 1032 are coupled to a resistance such as a patient. In additional examples, the H-bridge circuit 1026 is to provide a sawtooth shaped waveform.

In some examples, at least one die of a solid state switch is thermally coupled to one of a conductive interconnect or a connection member. In the illustrated example, for example, a die 1028 is shown coupled to a conductive interconnect. As such, the conductive interconnect serves as a heat sink to sink heat away from the switch in use. Any of the electronic components 1014, 1016, 1018, 1020 and 1022 optionally include die coupled to connection members so that the connection member, and thus the stack 1002, serves to sink heat from one or more switches in use.

Figure 11:
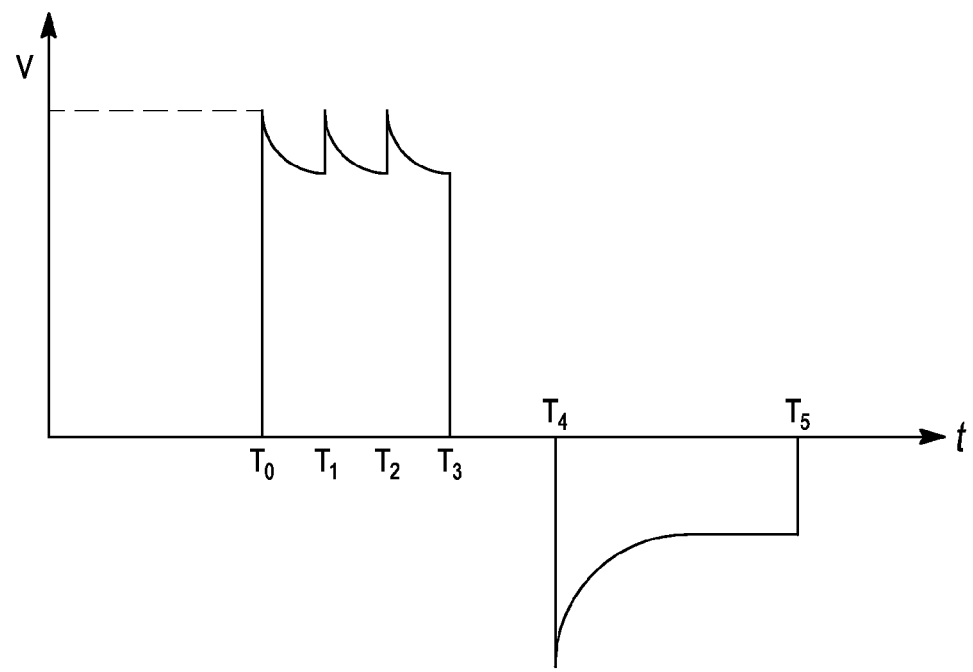
FIG. 11 is a chart showing voltage over time for the schematic and capacitor of FIG. 10.

FIG. 11 is a chart showing voltage over time for the schematic and capacitor of FIG. 10. At time T0, the H-Bridge circuit 1026 switches the capacitor to begin discharging. At this time, in examples in which electronic components 1014 and 1016 are switches, the switches are closed. At time T1, one of switches open to replenish he voltage available for discharge along the conductive interconnect 1017. At time T2, the other of switches is opened to again replenish the voltage available on the conductive interconnect 1017. At time T3 the H-bridge circuit 1026 switches to truncate voltage to the nodes 1030 and 1032. At time T4, the H-bridge circuit 1026 switches to reverse polarity to the nodes 1030 and 1032. At time T5, the H-bridge circuit 1026 again truncates voltage to the nodes 1030 and 1032.

Figure 12:
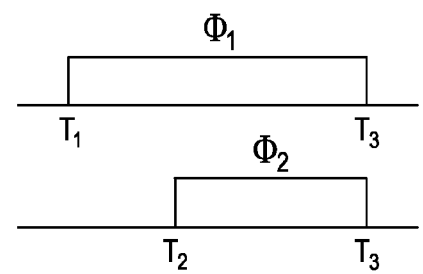
FIG. 12 is a diagram showing switching signals for switches of the schematic of FIG. 10.

FIG. 12 is a diagram showing switching signals for switches of the schematic of FIG. 10. The present subject matter is not limited to examples in which polarity is reversed, nor to examples in which voltage is truncated, and other waveforms are possible.

Figure 13:
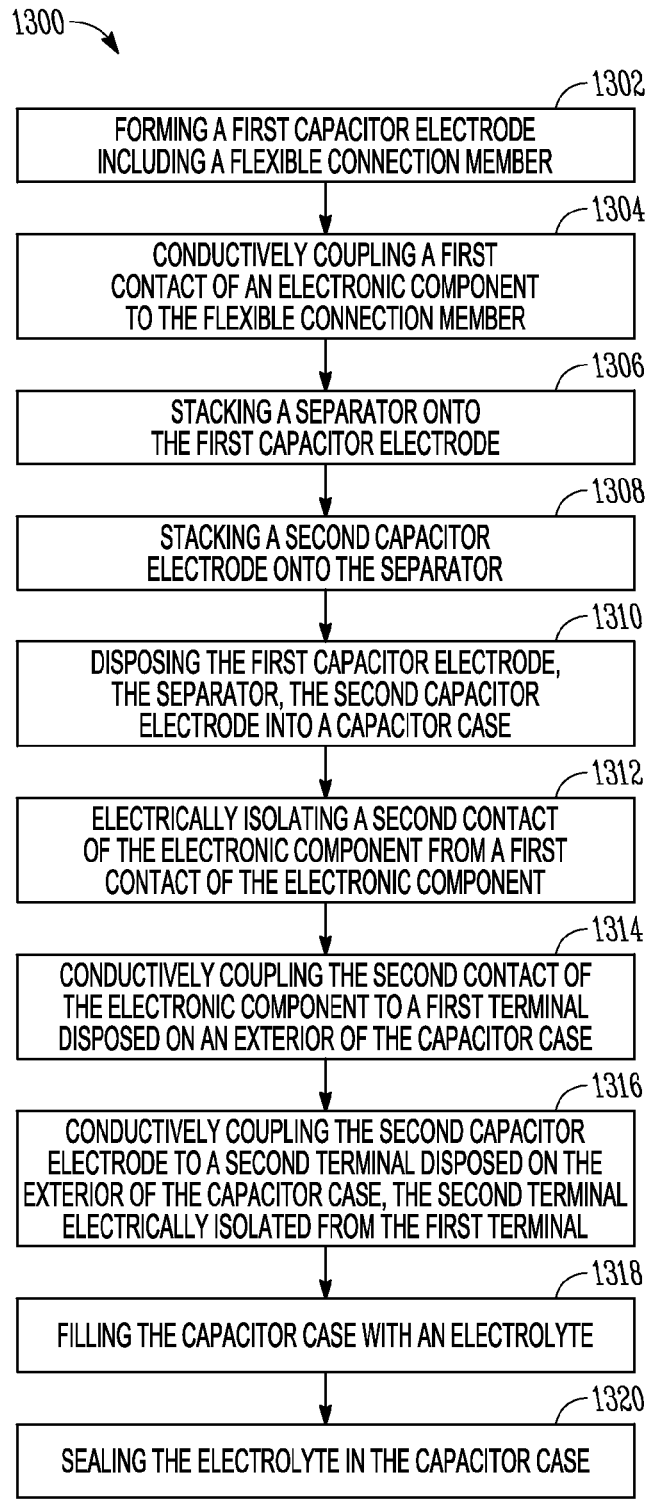
FIG. 13 is a method of forming a capacitor including an electronic component mounted on a capacitor, according to various examples.

FIG. 13 is a method 1300 of forming a capacitor including an electronic component disposed on a capacitor, according to various examples. At 1302, the method 1300 includes forming a first capacitor electrode including a flexible connection member. At 1304, the method 1300 includes conductively coupling a first contact of an electronic component to the connection member. At 1306, the method 1300 includes stacking a separator onto the first capacitor electrode. At 1308, the method 1300 includes stacking a second capacitor electrode onto the separator. At 1310, the method 1300 includes disposing the first capacitor electrode, the separator, and the second capacitor electrode into a capacitor case. At 1312, the method 1300 includes electrically isolating a second contact of the electronic component from a first contact of the electronic component. At 1314, the method 1300 includes conductively coupling the second contact of the electronic component to a first terminal disposed on an exterior of the capacitor case. At 1316, the method 1300 includes conductively coupling the second capacitor electrode to a second terminal disposed on the exterior of the capacitor case, the second terminal electrically isolated from the first terminal. At 1318, the method 1300 includes filling the capacitor case with an electrolyte. At method 1320, the method 1300 includes sealing the electrolyte in the capacitor case.

Additionally, various methods include forming the first capacitor electrode by sintering material onto a foil substrate. Additional optional methods include coupling an electronic component to the connection member including mounting a first electronic component terminal and a second electronic terminal each to the connection member, and excising the connection member to electrically isolate the first electronic component terminal from the second electronic component terminal. Additional optional methods include coupling a second electronic component to the connection member with respective terminals of the second electronic component electrically isolated from one another via a cut in the connection member.

Various examples are contemplated. A first example includes a capacitor case sealed to retain electrolyte. Electrolyte is disposed in the capacitor case, a capacitor electrode disposed in the capacitor case, an electronic component, other than the capacitor electrode, mounted to the capacitor electrode and disposed in the capacitor case, the electronic component including two contacts, with a first contact mounted onto the capacitor electrode and with a second contact mounted onto a terminal disposed on an exterior of the capacitor case and sealingly extending through the capacitor case, the first and second contacts electrically isolated from one another, a additional capacitor electrode disposed in the capacitor case, a separator disposed between the capacitor electrode and the additional capacitor electrode and a additional terminal is disposed on the exterior of the capacitor case and in electrical communication with the additional capacitor electrode, with the terminal and the additional terminal electrically isolated from one another.

A second example includes the first example, wherein the capacitor electrode includes a sintered portion.

A third example includes the second example, wherein the sintered portion is disposed on a foil substrate, and the electronic component is mounted on the foil substrate.

A fourth example includes any of the first through third examples, wherein the electronic component is mounted onto the capacitor electrode with surface mount technology ("SMT").

A fifth examples includes any of the first through fourth examples, wherein the electronic component is a resistor, and comprising a diode coupled to the resistor, with an anode of the diode coupled to the resistor and a cathode of the diode coupled with a conductor.

A sixth examples include any of the first through fifth examples, wherein the electronic component is a solid state switch, and the solid state switch includes a die that is thermally coupled to the capacitor electrode.

A seventh examples includes any of the first through sixth examples, wherein the capacitor electrode includes a sheet with a main body comprising a sintered portion, and a connection member extending away from the main body comprising a connection portion, with the electronic component mounted on the connection portion.

An eighth example includes any of the first through seventh examples, wherein the capacitor case includes a dish portion and a lid portion, with the electronic component mounted onto the dish portion.

A ninth example includes any of the first through eighth examples, wherein the capacitor electrode and the additional capacitor electrode are part of a first capacitor partition, and with the capacitor including at least a second partition including a third capacitor electrode coupled with a additional electronic component and a fourth capacitor electrode.

A tenth examples includes the ninth example, wherein the electric component is a diode with a first diode anode coupled to the first capacitor electrode, and the additional electric component is a second diode with a second diode anode coupled to the additional capacitor electrode, with a first diode cathode coupled with a second diode cathode with the first capacitor partition adapted to discharge in sequence with the second partition.

An eleventh example includes the tenth example, wherein the first capacitor partition and the second capacitor partition are adapted to discharge a sawtooth waveform.

A twelfth example of constructing a capacitor includes forming a first capacitor electrode including a flexible connection member, conductively coupling a first contact of an electronic component, other than the first capacitor electrode, to the flexible connection member, stacking a separator onto the first capacitor electrode, stacking a second capacitor electrode onto the separator, disposing the first capacitor electrode, the separator, and the second capacitor electrode into a capacitor case, electrically isolating a second contact of the electronic component from the first contact of the electronic component, conductively coupling the second contact of the electronic component to a first terminal disposed on an exterior of the capacitor case, conductively coupling the second capacitor electrode to a second terminal disposed on the exterior of the capacitor case, the second terminal electrically isolated from the first terminal, filling the capacitor case with an electrolyte and sealing the electrolyte in the capacitor case.

A thirteenth example includes the twelfth example, comprising forming the first capacitor electrode by sintering material onto a foil substrate.

A fourteenth examples includes the examples of any of the twelfth and thirteenth examples, wherein coupling an electronic component to the connection member includes mounting a first electronic component terminal and a second electronic component terminal each to the connection member, and excising the connection member to electrically isolate the first electronic component terminal from the second electronic component terminal.

A fifteenth examples includes the fourteenth examples, comprising coupling a second electronic component to the connection member with respective terminals of the second electronic component electrically isolated from one another via a cut in the connection member.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An apparatus, comprising:
   a capacitor case sealed to retain electrolyte;
   electrolyte disposed in the capacitor case;
   a capacitor electrode disposed in the capacitor case, the capacitor electrode includes a foil substrate;
   an electronic component, other than the capacitor electrode, mounted directly onto the capacitor electrode foil substrate and disposed in the capacitor case, the electronic component including two contacts, with a first contact mounted directly onto the capacitor electrode foil substrate and with a second contact mounted onto a terminal disposed on an exterior of the capacitor case and sealingly extending through the capacitor case, the first and second contacts electrically isolated from one another;
   an additional capacitor electrode disposed in the capacitor case;
   a separator disposed between the capacitor electrode and the additional capacitor electrode; and
   an additional terminal disposed on the exterior of the capacitor case and in electrical communication with the additional capacitor electrode, with the terminal and the additional terminal electrically isolated from one another, wherein the electronic component is a transformer disposed in the capacitor case and thermally coupled to the capacitor electrode.

2. The apparatus of claim 1, wherein the capacitor electrode includes a sintered portion.

3. The apparatus of claim 2, wherein the sintered portion is disposed on the foil substrate.

4. The apparatus of claim 2, wherein the electronic component is mounted onto the capacitor electrode with surface mount technology ("SMT").

5. The apparatus of claim 1, wherein the electronic component further includes a resistor.

6. The apparatus of claim 5, comprising a diode coupled to the resistor, with an anode of the diode coupled to the resistor and a cathode of the diode coupled with a conductor.

7. The apparatus of claim 1, wherein the electronic component further includes a solid state switch.

8. The apparatus of claim 7, wherein the solid state switch includes a die that is thermally coupled to the capacitor electrode.

9. A system, comprising:
   a hermetically sealed device housing;
   a battery disposed in the hermetically sealed device housing;
   a capacitor disposed in the hermetically sealed device housing, the capacitor comprising:
      a capacitor case sealed to retain electrolyte;
      electrolyte disposed in the capacitor case;
      a capacitor electrode disposed in the capacitor case, the capacitor electrode includes a foil substrate;
      an electronic component, other than the capacitor electrode, mounted directly onto the capacitor electrode substrate foil and disposed in the capacitor case, the electronic component including two contacts, with a first contact mounted directly onto the capacitor electrode foil substrate and with a second contact mounted onto a terminal disposed on an exterior of the capacitor case and sealingly extending through the capacitor case, the first and second contacts electrically isolated from one another;
      an additional capacitor electrode disposed in the capacitor case;
      a separator disposed between the capacitor electrode and the additional capacitor electrode; and
      a additional terminal disposed on the exterior of the capacitor case and in electrical communication with the additional capacitor electrode, with the terminal and the additional terminal electrically isolated from one another, and
   an electronic cardiac rhythm management circuit coupled to the battery and the capacitor and adapted to charge the capacitor with the battery and to discharge the capacitor to provide a therapeutic defibrillation pulse, wherein the electronic component is a transformer disposed in the capacitor case and thermally coupled to the capacitor electrode.

10. The system of claim 9, wherein the electronic component further includes a solid state switch.

11. The system of claim 10, wherein the capacitor electrode substrate foil comprises a sheet with a main body comprising a sintered portion, and a connection member extending away from the main body comprising a connection portion, with the electronic component mounted on the connection portion.

12. The system of claim 9, wherein the capacitor case includes a dish portion and a lid portion, with the electronic component mounted onto the dish portion.

13. The system of claim 9, wherein the capacitor electrode and the additional capacitor electrode are part of a first capacitor partition, and with the capacitor including at least a second capacitor partition including a third capacitor electrode coupled with an additional electronic component and a fourth capacitor electrode.

14. A system comprising:
   a hermetically sealed device housing;
   a battery disposed in the hermetically sealed device housing;
   a capacitor disposed in the hermetically sealed device housing, the capacitor comprising:
      a capacitor case sealed to retain electrolyte;
      electrolyte disposed in the capacitor case;
      a capacitor electrode disposed in the capacitor case, the capacitor electrode includes a foil substrate;
      an electronic component, other than the capacitor electrode, mounted to the capacitor electrode and disposed in the capacitor case, the electronic component including two contacts, with a first contact mounted onto the capacitor electrode and with a second contact mounted onto a terminal disposed on an exterior of the capacitor case and sealingly extending through the capacitor case, the first and second contacts electrically isolated from one another;
      an additional capacitor electrode disposed in the capacitor case;
      a separator disposed between the capacitor electrode and the additional capacitor electrode; and
      a additional terminal disposed on the exterior of the capacitor case and in electrical communication with the additional capacitor electrode, with the terminal and the additional terminal electrically isolated from one another, and
   an electronic cardiac rhythm management circuit coupled to the battery and the capacitor and adapted to charge the capacitor with the battery and to discharge the capacitor to provide a therapeutic defibrillation pulse,
   wherein the capacitor electrode and the additional capacitor electrode are part of a first capacitor partition, and with the capacitor including at least a second capacitor partition including a third capacitor electrode coupled with an additional electronic component and a fourth capacitor electrode,
   wherein the electric component is a diode with a first diode anode coupled to the capacitor electrode, and the additional electric component is a second diode with a second diode anode coupled to the additional capacitor electrode, with a first diode cathode coupled with a second diode cathode wherein the first capacitor partition is adapted to discharge in sequence with the second partition.

15. The system of claim 14, wherein the first capacitor partition and the second capacitor partition are adapted to discharge a sawtooth waveform.

* * * * *